United States Patent
Gharda

(10) Patent No.: US 9,062,000 B2
(45) Date of Patent: *Jun. 23, 2015

(54) BIS-QUINALDINE COMPOUND AND A PROCESS FOR PREPARING THE SAME

(71) Applicant: Keki Hormusji Gharda, Maharashtra (IN)

(72) Inventor: Keki Hormusji Gharda, Maharashtra (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/353,639

(22) PCT Filed: Oct. 22, 2012

(86) PCT No.: PCT/IN2012/000696
§ 371 (c)(1),
(2) Date: Apr. 23, 2014

(87) PCT Pub. No.: WO2013/098837
PCT Pub. Date: Jul. 4, 2013

(65) Prior Publication Data
US 2014/0296529 A1    Oct. 2, 2014

(30) Foreign Application Priority Data
Oct. 24, 2011  (IN) .......................... 2990/MUM/2011

(51) Int. Cl.
*C07D 215/40*  (2006.01)
*C07D 215/18*  (2006.01)
(52) U.S. Cl.
CPC ............ *C07D 215/40* (2013.01); *C07D 215/18* (2013.01)
(58) Field of Classification Search
CPC ... C07D 215/40; C07D 215/15; A01B 12/006
USPC ........................................................ 546/171
See application file for complete search history.

(56) References Cited

U.S. PATENT DOCUMENTS

| 5,106,980 A | 4/1992 | Ort et al. |
| 2014/0288311 A1* | 9/2014 | Gharda ........................ 546/167 |

FOREIGN PATENT DOCUMENTS

| CN | 1763013 A | 4/2006 |
| DE | 429176 | 5/1926 |
| EP | 0463477 A1 | 1/1992 |
| GB | 395063 | 7/1933 |
| GB | 895090 | 5/1962 |
| GB | 980394 | 1/1965 |

OTHER PUBLICATIONS

Miyatake Masayoshi, Ehashi Shigeyuki, Study on Quinophthalone Pigments, Shikizai Kyokaishi, Jan. 1, 1971,p. 316-324, vol. 44, Japan.
M.M. Sidky, A. A. El-Kateb, Uber 6,6'-Dichinolyl-Derivate, Archiv Der Pharmazie, 1968, pp. 571-573, vol. 301, No. 8.
Francis H. Case, The Synthesis of 2,2 and 5,5-Bi(1,10-phenanthroline) (1), J. Heterocyclic Chem., 1964, p. 112, vol. 1, No. 2.

* cited by examiner

*Primary Examiner* — D M Seaman
(74) *Attorney, Agent, or Firm* — Muncy, Geissler, Olds & Lowe, P.C.

(57) ABSTRACT

The present disclosure relates to a bis-quinaldine compound of formula I and a process for the same.

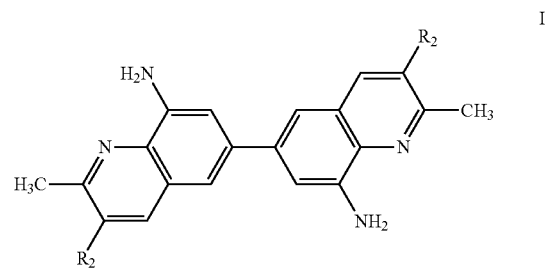

wherein $R_2$ is a substituent selected from the group consisting of H, $C_1$-$C_{20}$ straight or branched chain alkyl substituents, aromatic substituents, aliphatic substituents, combinations thereof and the like.

12 Claims, No Drawings

BIS-QUINALDINE COMPOUND AND A PROCESS FOR PREPARING THE SAME

CROSS REFERENCE TO RELATED APPLICATIONS

This application is a national stage of International Application No.: PCT/IN2012/000696, which was filed on Oct. 22, 2012, and which claims priority to 2990/MUM/2011 which was filed on Oct. 24, 2011, and which are both herein incorporated by reference.

FIELD OF THE DISCLOSURE

The present disclosure relates to quinaldine compounds and a process for preparing the same.

BACKGROUND

Quinaldine or 2-methylquinoline is a simple derivative of a heterocyclic compound quinoline. Quinaldines are known to have varied applications which include anti-malarial drugs, dyes, food colorants, pH indicators, pharmaceuticals and pigments.

Pigments are known to have wide applications in human life such as coatings, paints, papers, adhesives, latexes, toners, textiles, fibers, plastics, cosmetics and inks. A large numbers of organic and inorganic yellow pigments are available. They differ by their brightness of shade, opacity, fastness requirements, physiological properties, and economic considerations. These properties influence the choice of the pigments depending on the end application. As well as being used in yellow paints, yellow pigments are also used in oranges, greens and browns. Quinophthalone pigment is an organic yellow pigment used as a chrome replacement in high quality finishes.

Quinophthalone pigment is prepared from quinaldine compounds. Shikizai Kyokaishi, 44 (1971), 316-324 discloses preparation of quinophthalone pigments using bis quinaldines.

German Patent No. 429176 discloses a process of preparing mono quinophthalones by reacting 3-hydroxy quinaldine with anhydride/imide of dicarboxylic acid followed by either halogenation or sulphonation reaction at 3-hydroxy position.

U.S. Pat. No. 5,106,980 discloses a process of preparing mono quinophthalones by condensing 8-aminoquinaldine with an optionally substituted phthalic anhydride in presence of molten benzoic acid as diluent at a temperature ranging between 123° C. to 200° C.

A method for preparation of bis quinophthalones having hydrogen or chlorine or methyl substituent at 8-position is disclosed in an article titled "Study on Quinophthalone Pigments" Shikizai Kyokaishi, 44 (1971), 316-324.The method disclosed in the article comprises two steps: i) fusing phthalic anhydride; and ii) adding 6, 6'-bis quinaldine and heating at 170° C. to 180° C. for 6 hours to 12 hours.

Quinaldine is generally prepared from aniline and paraldehyde via Skraup synthesis or from aniline and crotonaldehyde via Doebner-von Miller variation of the Skraup reaction or extracted from coal tar.

CN 1763013 discloses Preparation of 8-amino-quinaldine from 8-nitro-2-methyl-quinoline by hydrogenation in benzene solvent in the presence of Pd/C catalyst.

Shikizai Kyokaishi, 44 (1971), 316-324 "Study on Quinophthalone Pigments", discloses a method of preparation of 8,8'-dimethyl-6,6'-bis-quinaldine and 8,8'-dichloro-6, 6'-bis quinaldine. According to the disclosure, benzidine is reacted with crotonaldehyde in presence of concentrated sulfuric acid, nitrobenzene-m-sulfonic acid sodium and ammonium vanadate at about 110° C. for a period of about 6 hours. However, the yield of bis-quinaldines is on a lower side in the range of 25% to 66%. Shikizai Kyokaishi, 44 (1971), 316-324 also discloses preparation of bis-quinophthalone pigments using bis quinaldines.

British Patent 395063 discloses a process for preparing quinaldines, which consists of heating amine and crotonaldehyde in presence of ammonium vanadate and oxidizing agent such as nitrobenzene sulfonic acid. Nitrobenzene sulfonic acid is in-situ generated from nitrobenzene and sulfuric acid.

Another, British Patent 895090 discloses a process for preparing anti-bacterial product containing N4,N4-alkylene-N1,N1-alkylene-bis-4-amino-quinaldinium dihalides, which comprises reacting 4-halo quinaldine or 4-halo quinaldiniuim halide with α,ω-diaminoalkane and reacting the resulting N4,N4-bis-quinaldinium compound with α,ω-dihaloalkane.

Still another British Patent 980394 discloses the quinaldinium derivative and its method of preparation.

However, Bis-quinophthalones disclosed in Shikizai Kyokaishi, 44 (1971), 316-324, shows remarkable color fading when exposed for longer hours and are poor light resistant.

The mono-quinophthalone and bis-quinophthalone of the prior art typically, suffer from drawbacks such as poor light resistance, poor solvent resistance, poor hue and less stability.

Research on new quinophthalone compounds which obviates the drawback of the prior art is being carried out. Co-pending application 2991/MUM/2011 deals with new quinophthalone pigments.

Accordingly, there is felt a need to develop new quinaldine compounds for preparing quinophthalone compounds that obviates the drawback of the prior art as disclosed above.

OBJECTS OF THE DISCLOSURE

It is an object of the present disclosure to provide novel quinaldine compounds for preparing novel quinophthalone pigments.

It is still another object of the present disclosure to provide a feasible process for preparing bis-quinaldine compounds.

SUMMARY

The present disclosure provides a process for preparing a bis-quinaldine compound of formula I, said process comprising the following steps:

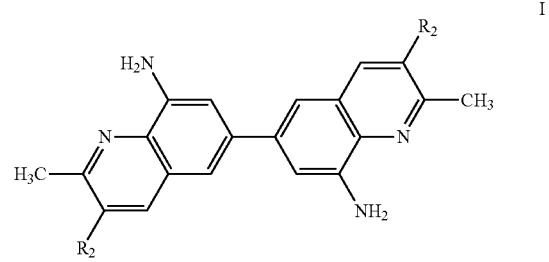

wherein $R_2$ is substituent selected from the group consisting of H, $C_1$-$C_{20}$ straight or branched chain alkyl substituents, aromatic substituents, aliphatic substituents, combinations thereof and the like, a) condensing a compound of Formula (II)

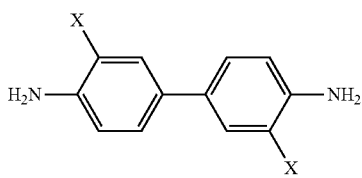

wherein X is preferably Br or Cl,
with a compound of Formula (III),

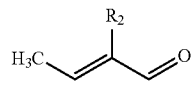

wherein R$_2$ is a substituent selected from the group consisting of H, C$_1$-C$_{20}$ straight or branched chain alkyl substituents, aromatic substituents, aliphatic substituents, combinations thereof and the like
to obtain an intermediate compound of Formula (IV), and;

(Formula IV)

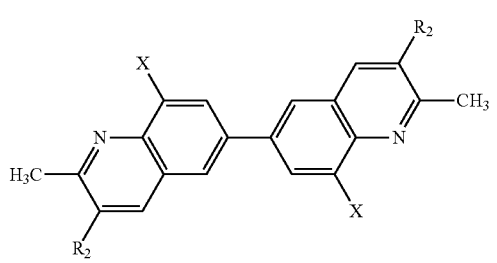

wherein X=preferably Br or Cl; and R$_2$ is substituent selected from the group consisting of H, C$_1$-C$_{20}$ straight or branched chain alkyl substituents, aromatic substituents, aliphatic substituents, combinations thereof and the like;

ii) reacting the compound of Formula (IV) with a nitrogen compound to obtain the compound of Formula (I).

Typically, the step of condensation (i) is carried out in the presence of sulfuric acid and sodium iodide at a temperature in the range of 25° C. to 150° C.

Typically, the amount of sulfuric acid is in the range of 10.0 moles to 20.0 moles per mole of a compound of Formula (II).

Typically, the amount of sodium iodide is in the range of 5.0 gm to 20.0 gm per mole of the compound of Formula (II).

Typically, the amount of the compound of formula (III) is in the range of 2.0 moles to 5.0 moles per mole of the compound of Formula (II).

Typically, the step of reacting nitrogen compound with the compound of Formula (IV) is carried out in the presence of cuprous chloride at a temperature in the range of 150° C. to 250° C. and at a pressure range of 25 to 50 kg/cm2.

In one embodiment of the present disclosure the step of reacting nitrogen compound with the compound of Formula (IV) is optionally carried out in the presence of polar solvent selected from the group consisting of N-methyl Pyrrolidone, Dimethylacetamide and Dimethylformamide.

Typically, the nitrogen compound is ammonia in the range of 20.0 moles to 60.0 moles per mole of a compound of Formula (IV).

Typically, the amount of cuprous chloride is in the range of 20.0 gm to 60.0 gm per mole of a compound of Formula (IV).

DETAILED DESCRIPTION

The present disclosure provides a bis-quinaldine compound of formula I

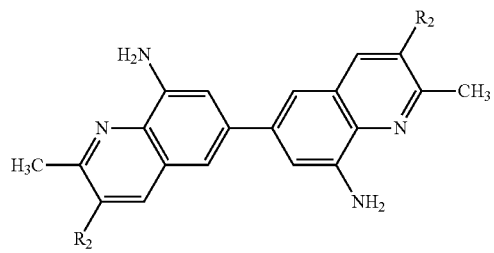

wherein R$_2$ is substituent selected from the group consisting of H, C$_1$-C$_{20}$ straight or branched chain alkyl substituents, aromatic substituents, aliphatic substituents, combinations thereof and the like.

Another aspect of the present disclosure provides a process for preparing the compound of formula I. The process involves the step of condensing a compound of Formula (II)

II

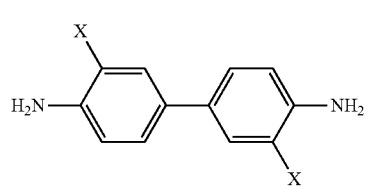

wherein X is preferably Br or Cl,
with a compound of Formula (III), to obtain an intermediate compound of Formula (IV).

(Formula III)

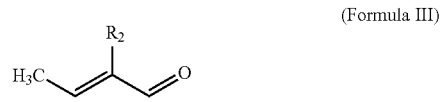

wherein R$_2$ is a substituent selected from the group consisting of H, C$_1$-C$_{20}$ straight or branched chain alkyl substituents, aromatic substituents, aliphatic substituents, combinations thereof and the like (Formula IV)

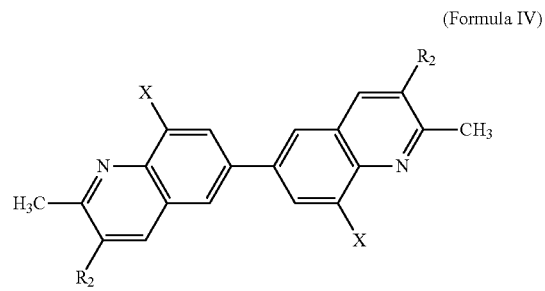

wherein X=preferably Br or Cl; and $R_2$ is substituent selected from the group consisting of H, $C_1$-$C_{20}$ straight or branched chain alkyl substituents, aromatic substituents, aliphatic substituents, combinations thereof and the like.

The compound of Formula (IV) is further reacted with a nitrogen compound to obtain the compound of Formula (I).

The step of condensation (i) is carried out in the presence of mineral acids, preferably sulfuric acid and sodium iodide at a temperature in the range of 25° C. to 150° C. The amount of sulfuric acid used in the range of about 10.0 moles to about 20.0 moles per mole of a compound of Formula (II). The amount of sodium iodide used is in the range of about 5.0 gm to about 20.0 gm per mole of the compound of Formula (II).

The amount of the compound of formula (III) used is in the range of about 2.0 moles to about 5.0 moles per mole of the compound of Formula (II).

The step of reacting nitrogen compound with the compound of Formula (IV) is carried out in the presence of cuprous chloride and with or without polar solvent like N-methyl Pyrrolidone, Dimethylacetamide, and Dimethylformamide etc, at a temperature in the range of 150° C. to 250° C. and at a pressure range of 25 to 50 kg/cm2. The nitrogen compound is ammonia in the range of about 20.0 moles to about 60.0 moles per mole of a compound of Formula (IV). The amount of cuprous chloride is in the range of about 20.0 gm to about 60.0 gm per mole of a compound of Formula (IV).

In a preferred embodiment of the present disclosure, the compound of formula II is 3,3'-dichlorobenzidine.

3,3'-dichlorobenzidine is condensed with crotonaldehyde (Formula III) to obtain a bis quinaldine compound 8,8'-dichloro-6,6'-bis-quinaldine (Formula IV). The dichloro bis quinaldine compound is further reacted with nitrogen compound, preferably ammonia to obtain diamino derivative of bis quinaldine (Formula I).

The disclosure is further illustrated by the following examples that should not be construed as limiting.

EXAMPLE 1

Preparation of Bis-8-amino quinaldine
(8,8'-diamino-6,6'-bis-quinaldine)

Step 1: Preparation of Bis-8-chloro-quinaldine (8,8'-dichloro-6,6'-bis-quinaldine)

253 gm (1 mole) of 3,3'-dichlorobenzindine was added to 1610 gm (11.5 mol) of 70% (wt/wt) sulfuric acid solution and heated to 50° C. for 1 hour under stirring to obtain a mixture. To the resulting mixture, a solution of 7 gm of Sodium Iodide in 10 ml of water was slowly added and the mixture was heated to 100° C. for 1 hour. To this mixture, 247 gm crotonaldehyde (85%) was slowly added at 100° C. over a period of 3.5 hours. Scrubbing of the gas from condenser was maintained during addition. After addition the reaction mass was stirred at 101° C. for about 7 hours and further cooled to 50° C. The reaction mass was quenched by pouring on 5000 gm ice water while maintaining the temperature between 30° C. to 40° C. Subsequently, caustic lye was added to maintain the pH at 1.00. The reaction mass was filtered through hyflow bed and washed with water. The mother liquor obtained was neutralized by caustic lye and filtered. The cake so obtained was washed with hot water and dried to yield Bis-8-chloro-quinaldine (264 gm, 75%).

EXAMPLE 2

253 gm (1 mole) of 3,3'-dichlorobenzindine was added to 2100 gm (15 mol) of 70% (wt/wt) sulfuric acid solution and heated to 50° C. for 1 hour under stirring to obtain a mixture. To the resulting mixture, a solution of 7 gm of Sodium Iodide in 10 ml of water was slowly added and heated to 100° C. for 1 hour. To this solution, 247 gm crotonaldehyde (85%) was slowly added at 100° C. over a period of 3.5 hours. Scrubbing of the gas from condenser was maintained during addition. After addition the reaction mass was stirred at 101° C. for about 7 hours and cooled to 50° C. The reaction mass was quenched by pouring on 5000 gm ice water while maintaining the temperature between 30° C. to 40° C. Subsequently, caustic lye was added to maintain the pH at 1.00. The reaction mass was filtered through hyflow bed and washed with water. The mother liquor obtained was neutralized by caustic lye and filtered. The cake so obtained was washed with hot water and dried to yield Bis-8-chloro-quinaldine (282 gm, 80%).

EXAMPLE 3

253 gm of 3,3'-dichlorobenzindine was added to 1610 gm of 70% (wt/wt) sulfuric acid solution and heated to 50° C. for 1 hour under stirring to obtain a mixture. To the resulting mixture, a solution of 7 gm of Sodium Iodide in 10 ml of water was slowly added and heated to 80° C. for 1 hour. To this solution, 247 gm crotonaldehyde (85%) was slowly added at 80° C. over a period of 3.5 hours. Scrubbing of the gas from condenser was maintained during addition. After completion of addition the reaction mass was stirred at 80° C. for about 7 hours and cooled to 50° C. The reaction mass was quenched by pouring on 5000 gm ice water while maintaining the temperature between 30° C. to 40° C. Subsequently, caustic lye was added to maintain the pH at 1.00. The reaction mass was filtered through hyflow bed and washed with water. The mother liquor obtained was neutralized by caustic lye and filtered. The cake so obtained was washed with hot water and dried to yield Bis-8-chloro-quinaldine (247 gm, 70%).

EXAMPLE 4

253 gm of 3,3'-dichlorobenzindine was added to 1610 gm of 70% (wt/wt) sulfuric acid solution and heated to 50° C. for 1 hour under stirring to obtain a mixture. To the resulting mixture, a solution of 12 gm of Sodium Iodide in 10 ml of water was slowly added and heated to 100° C. for 1 hour. To this solution, 247 gm crotonaldehyde (85%) was slowly added at 100° C. over a period of 3.5 hours. Scrubbing of the gas from condenser was maintained during addition. After completion of addition the reaction mass was stirred at 101° C. for about 7 hours and cooled to 50° C. The reaction mass was quenched by pouring on 5000 gm ice water while maintaining the temperature between 30° C. to 40° C. Subsequently, caustic lye was added to maintain the pH at 1.00. The reaction mass was filtered through hyflow bed and washed with water. The mother liquor obtained was neutralized by caustic lye and filtered. The cake so obtained was washed with hot water and dried to yield 282 gm (80%) Bis-8-chloro-quinaldine.

EXAMPLE 5

253 gm of 3,3'-dichlorobenzindine was added to 1610 gm of 70% (wt/wt) sulfuric acid solution and heated to 50° C. for 1 hour under stirring to obtain a mixture. To the resulting mixture, a solution of 17 gm of Sodium Iodide in 10 ml of water was slowly added and heated to 100° C. for 1 hour. To this solution, 247 gm crotonaldehyde (85%) was slowly added at 100° C. over a period of 3.5 hours. Scrubbing of the gas from condenser was maintained during addition. After completion of addition the reaction mass was stirred at 101° C. for about 7 hours and cooled to 50° C. The reaction mass was quenched by pouring on 5000 gm ice water while maintaining the temperature between 30° C. to 40° C. Subsequently, caustic lye was added to maintain the pH at 1.00. The reaction mass was filtered through hyflow bed and washed with water. The mother liquor obtained was neutralized by caustic lye and filtered. The cake so obtained was washed with hot water and dried to yield 286 gm (81%) Bis-8-chloro-quinaldine.

EXAMPLE 6

253 gm of 3,3'-dichlorobenzindine was added to 1610 gm of 70% (wt/wt) sulfuric acid solution and heated to 50° C. for 1 hour under stirring to obtain a mixture. To the resulting mixture, a solution of 12 gm of Sodium Iodide in 10 ml of water was slowly added and heated to 100° C. for 1 hour. To this solution, 329 gm (4 mol) crotonaldehyde (85% purity) was slowly added at 100° C. over a period of 3.5 hours. Scrubbing of the gas from condenser was maintained during addition. After completion of addition the reaction mass was stirred at 101° C. for about 7 hours and cooled to 50° C. The reaction mass was quenched by pouring on 5000 gm ice water while maintaining the temperature between 30° C. to 40° C. Subsequently, caustic lye was added to maintain the pH at 1.00. The reaction mass was filtered through hyflow bed and washed with water. The mother liquor obtained was neutralized by caustic lye and filtered. The cake so obtained was washed with hot water and dried to yield 272 gm (77%) Bis-8-chloro-quinaldine.

Step 2: Preparation of Bis-8-amino-quinaldine

EXAMPLE 7

In an autoclave a mixture of 100 gm (0.28 mol) of Bis-8-chloroquinaldine and 1000 ml of ammonia (14N) (14 mol) in the ratio 1:50 mol/mol and 15 gm of cuprous chloride (53.5 gm/mol) in 500 ml of N-methylpyrrolidone were charged to obtain a mixture. The obtained mixture was heated to 202-205° C. and maintained for 4 to 5 hours at a pressure up to 45 kg/cm$^2$. The reaction was stirred for about 27 hours at same temperature and pressure conditions. The reaction mixture was cooled to 50° C. after confirming the completion of reaction by HPLC. The reaction mass was then filtered, washed with water and dried to yield Bis-8-amino quinaldine (80 gm, 90%).

EXAMPLE 8

In an autoclave a mixture of 100 gm (0.28 mol) of Bis-8-chloroquinaldine, 1000 ml of ammonia (14N)) (14 mol) in the ratio 1:50 mol/mol and 15 gm of cuprous chloride (53.5 gm/mol) in 500 ml of N-methylpyrrolidone were charged to obtain a mixture. The obtained mixture was heated to 180° C.-182° C. and maintained for 4 to 5 hours at a pressure up to 30 kg/cm$^2$. The reaction was stirred for about 32 hours at same temperature and pressure conditions. The reaction mixture was cooled to 50° C. after confirming the completion of reaction by HPLC. The reaction mass was then filtered, washed with water and dried to yield Bis-8-amino quinaldine (66 gm, 75%).

EXAMPLE 9

In an autoclave a mixture of 100 gm (0.28 mol) of Bis-8-chloroquinaldine, 1000 ml of ammonia (8.4N)) (8.4 mol) in the ratio 1:30 mol/mol and 15 gm of cuprous chloride in 500 ml of N-methylpyrrolidone were charged to obtain a mixture. The obtained mixture was heated to 215-217° C. and maintained for 4 to 5 hours at a pressure up to 45 kg/cm$^2$. The reaction was stirred for about 32 hours at same temperature and pressure conditions. The reaction mixture was cooled to 50° C. after confirming the completion of reaction by HPLC. Reaction is slow and is completed in 48 hrs for completion to yield 74.74 gm (85%) Bis-8-amino quinaldine.

EXAMPLE 10

In an autoclave a mixture of 100 gm (0.28 mol) of Bis-8-chloroquinaldine, 1000 ml of ammonia (14N)) (14 mol) in the ratio 1:50 mol/mol and 15 gm of cuprous chloride in 500 ml of Dimethyl acetamide were charged to obtain a mixture. The obtained mixture was heated to 202-205° C. and maintained for 4 to 5 hours at a pressure up to 45 kg/cm$^2$. The reaction was stirred for about 27 hours at same temperature and pressure conditions. The reaction mixture was cooled to 50° C. after confirming the completion of reaction by HPLC. The reaction mass was then filtered, washed with water and dried to yield Bis-8-amino quinaldine (70.33 gm, 80%).

The numerical values mentioned for the various physical parameters, dimensions or quantities are only approximations and it is envisaged that the values higher/lower than the numerical values assigned to the parameters, dimensions or quantities fall within the scope of the invention, unless there is a statement in the specification specific to the contrary. Wherever a range of values is specified, a value up to 10% below and above the lowest and highest numerical value respectively, of the specified range, is included in the scope of the invention.

In view of the wide variety of embodiments to which the principles of the present invention can be applied, it should be understood that the illustrated embodiments are exemplary only. While considerable emphasis has been placed herein on the particular features of this invention, it will be appreciated that various modifications can be made, and that many changes can be made in the preferred embodiments without departing from the principle of the invention. These and other modifications in the nature of the invention or the preferred embodiments will be apparent to those skilled in the art from the disclosure herein, whereby it is to be distinctly understood that the foregoing descriptive matter is to be interpreted merely as illustrative of the invention and not as a limitation.

The invention claimed is:

1. A process for preparing a bis-quinaldine compound of formula I:

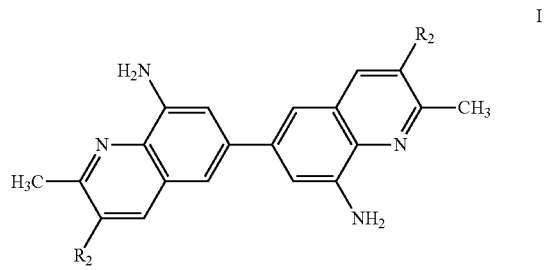

wherein R$_2$ is substituent selected from the group consisting of H, C$_1$-C$_{20}$ straight or branched chain alkyl substituents, aromatic substituents, aliphatic substituents, and combinations thereof, said process comprising the following steps:

a. condensing a compound of Formula (II),

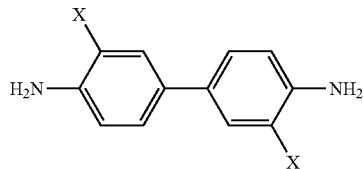

wherein X is preferably Br or Cl,
with a compound of Formula (III),

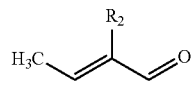

wherein $R_2$ is substituent selected from the group consisting of H, $C_1$-$C_{20}$ straight or branched chain alkyl substituents, aromatic substituents, aliphatic substituents, and combinations thereof
to obtain an intermediate compound of Formula (IV),

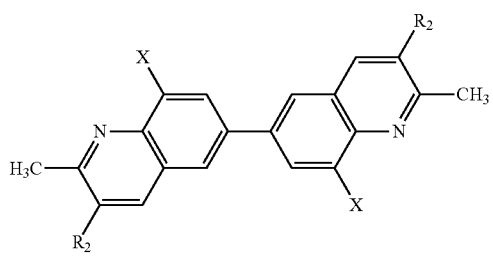

(Formula IV)

wherein X=Br or Cl; and $R_2$ is substituent selected from the group consisting of H, $C_1$-$C_{20}$ straight or branched chain alkyl substituents, aromatic substituents, aliphatic substituents, and combinations thereof;
and;

b. reacting the compound of Formula (IV) with a nitrogen compound to obtain a compound of Formula (I).

2. The process as claimed in claim 1, wherein the step of condensation (a) is carried out in the presence of sulfuric acid and sodium iodide at a temperature in the range of 25° C. to 150° C.

3. The process as claimed in claim 2, wherein the amount of sulfuric acid is in the range of 10.0 moles to 20.0 moles per mole of a compound of Formula (II).

4. The process as claimed in claim 2, wherein the amount of sodium iodide is in the range of 5.0 gm to 20.0 gm per mole of the compound of Formula (II).

5. The process as claimed in claim 1, wherein the amount of the compound of formula (III) is in the range of 2.0 moles to 5.0 moles per mole of the compound of Formula (II).

6. The process as claimed in claim 1, wherein the step of reacting nitrogen compound with the compound of Formula (IV) is carried out in the presence of cuprous chloride at a temperature in the range of 150° C. to 250° C. and at a pressure range of 25 to 50 kg/cm2.

7. The process as claimed in claim 1, wherein the nitrogen compound is ammonia in the range of 20.0 moles to 60.0 moles per mole of a compound of Formula (IV).

8. The process as claimed in claim 6, wherein the amount of cuprous chloride is in the range of 20.0 gm to 60.0 gm per mole of a compound of Formula (IV).

9. The process as claimed in claim 1, wherein the step of reacting the nitrogen compound with the compound of Formula (IV) is optionally carried out in the presence of a polar solvent selected from the group consisting of N-methylPyrrolidone, Dimethylacetamide and Dimethylformamide.

10. The process as claimed in claim 1, wherein the compound of formula IV is 8,8'-dichloro-6,6'-bis-quinaldine.

11. A compound of formula I prepared in accordance with the claim 1, wherein, $R_2$ is H.

12. The process as claimed in claim 1, wherein the compound of formula I is 8,8'-diamino-6,6'-bis-quinaldine.

\* \* \* \* \*